(12) United States Patent  (10) Patent No.: US 7,509,879 B2
Rieder et al.  (45) Date of Patent: Mar. 31, 2009

(54) VIBRATION-TYPE MEASUREMENT PICKUP AND ITS MEASURING TUBE

(75) Inventors: Alfred Rieder, Landshut (DE); Wolfgang Drahm, Freising (DE)

(73) Assignee: Endress + Hauser Flowtec AG, Reinach (CH)

( * ) Notice: Subject to any disclaimer, the term of this patent is extended or adjusted under 35 U.S.C. 154(b) by 0 days.

(21) Appl. No.: 10/580,247

(22) PCT Filed: Nov. 4, 2004

(86) PCT No.: PCT/EP2004/012479

§ 371 (c)(1), (2), (4) Date: May 4, 2007

(87) PCT Pub. No.: WO2005/050144

PCT Pub. Date: Jun. 2, 2005

(65) Prior Publication Data

US 2007/0277624 A1  Dec. 6, 2007

(30) Foreign Application Priority Data

Nov. 20, 2003 (DE) ................................ 103 54 373

(51) Int. Cl.
*G01F 1/84* (2006.01)
(52) U.S. Cl. ................................. 73/861.357
(58) Field of Classification Search ..................................
73/861.355–861.357
See application file for complete search history.

(56) References Cited

U.S. PATENT DOCUMENTS 3,218,851 A * 11/1965 Sipia ...................... 73/861.357

(Continued)

FOREIGN PATENT DOCUMENTS

DE  36 32 800 A1  4/1988

(Continued)

*Primary Examiner*—Harshad Patel
(74) *Attorney, Agent, or Firm*—Bacon & Thomas, PLLC (57) ABSTRACT

A measurement pickup, or transducer, includes at least one measuring tube for the conveying of a fluid. The measuring tube has an inlet end and an outlet end and vibrates at least at times. For enabling the fluid to be measured to flow through the measuring tube, the measuring tube communicates, via a first tube segment opening into the inlet end and via a second tube segment opening into the outlet end, with a pipeline connected therewith. For the oscillatable holding of the measuring tube, the measurement pickup further includes a support element having a first end piece containing a passageway for the securement of the first tube segment and having a second end piece containing a passageway for the securement of the second tube segment. Each of the two tube segments extends through its respective one of the two passageways and each of the two passageways has an inner diameter, which is greater than an outer diameter of its associated tube segment, so that an intermediate space is formed between each of the associated tube segments and end pieces. The measurement pickup further includes at least one, preferably metal, first spring element pushed onto one of the two tube segments. The spring element fills the intermediate space formed between tube segment and end piece at least partially, with the spring element being arranged in the intermediate space in such a manner that it contacts, at least sectionally, both its associated tube segment and also its associated end piece in such a manner that it is subjected, at least sectionally, to radially acting, deformation forces. As a result of elastic deformations accompanying such deformation forces, the spring element is held pressed against the associated tube segment and the associated end piece, whereby such tube segment is locked securely in the associated passageway.

13 Claims, 4 Drawing Sheets

U.S. PATENT DOCUMENTS

| | | | |
|---|---|---|---|
| 3,261,205 A * | 7/1966 | Sipia | 73/861.357 |
| 4,354,377 A | 10/1982 | Stansfeld | |
| 5,398,554 A * | 3/1995 | Ogawa et al. | 73/861.357 |
| 5,501,106 A * | 3/1996 | Lew et al. | 73/861.356 |
| 5,637,804 A * | 6/1997 | Hansen | 73/861.357 |
| 5,691,485 A * | 11/1997 | Endo et al. | 73/861.357 |
| 6,158,290 A * | 12/2000 | Hussain et al. | 73/861.357 |
| 6,336,369 B1 * | 1/2002 | Gomi et al. | 73/861.357 |
| 6,343,517 B1 | 2/2002 | Van Cleve | |
| 6,397,684 B1 * | 6/2002 | Van Cleve | 73/861.357 |
| 6,397,685 B1 * | 6/2002 | Cook et al. | 73/861.357 |
| 6,412,354 B1 * | 7/2002 | Birchak et al. | 73/861.356 |
| 6,487,917 B1 * | 12/2002 | Van Cleve et al. | 73/861.357 |

FOREIGN PATENT DOCUMENTS

| | | |
|---|---|---|
| DE | 41 00 006 A1 | 7/1992 |
| EP | 0 317 340 A2 | 5/1989 |
| JP | 09325060 A | 12/1997 |
| JP | 10160541 A | 6/1998 |
| JP | 10221148 A | 8/1998 |
| JP | 11023340 A | 1/1999 |
| WO | WO 96/08697 | 3/1996 |
| WO | WO 01/02815 A1 | 1/2001 |
| WO | WO 01/02816 A2 | 1/2001 |

* cited by examiner

VIBRATION-TYPE MEASUREMENT PICKUP AND ITS MEASURING TUBE

FIELD OF THE INVENTION

The invention relates to a vibration-type measurement pickup, or transducer. Especially, the invention is concerned with the securement of measuring tubes of such vibration-type measurement pickups (especially mass flow pickups working on the basis of the Coriolis principle) in support elements serving for the oscillatable holding of the measuring tubes.

BACKGROUND OF THE INVENTION

For the measuring, or registering, of a process variable of a media flowing in pipelines, especially for the registering of flow-dynamic and/or rheological, measured variables of fluids, inline measuring devices working according to the most varied of physical principles are used in measurements and automation technology. For registering the particular process variable, for example a mass flow, a density and/or a viscosity of a fluid, the inline measuring device has a corresponding, most often physical-to-electrical, measurement pickup, or transducer, which is inserted into the course of the line conveying the medium and which serves for producing at least one measurement signal, especially an electrical measurement signal, representing, as accurately as possible, the primarily registered, process variable. The measurement pickup is, in such case, connected with the pipeline e.g. by means of flanges, tightly against leakage of the medium, especially pressure-tightly, and, mostly, also lastingly.

For operating the measurement pickup, especially also for the further processing or evaluating of the at least one measurement signal, such is additionally attached to a corresponding measuring device electronics. In the case of inline measuring devices of the described type, the measuring device electronics is, in turn, usually connected via an attached data transmission system, with other inline measuring devices and/or with appropriate process control computers, to which they transmit the measured signals e.g. via (4 mA to 20 mA)-current loops and/or digital data bus. Serving often, in such case, for data transmission systems are, especially serial, fieldbus systems, such as e.g. PROFIBUS-PA, FOUNDATION FIELDBUS, together with the corresponding transmission protocols.

By means of the process control computer, the transmitted, measured-value signals can be processed further and visualized e.g. on monitors as corresponding measurement results and/or they can be converted into control signals for process-influencing actuators, such as e.g. solenoidal valves, electric motors, etc. For the accommodating of the measuring device electronics, such inline measuring devices include further an electronics housing, which, as proposed e.g. in WO-A 00/36 379, can be arranged remotely from the measurement pickup and connected with such only over a flexible line, or which, as shown e.g. also in EP-A 1 296 128 or WO-A 02/099363, is arranged directly on the measurement pickup, especially in the form of a measurement pickup housing, which houses the measurement pickup.

For the measuring of, especially, mass flows, e.g. flow rates, densities and/or viscosities of flowing media, inline measuring devices having a vibration-type measurement pickup for insertion into the course of a pipeline conveying the fluid to be measured have become established over a considerable period of time. Such inline measuring devices, or measurement pickups, their mechanical construction or also measuring and evaluation processes producing corresponding measurement signals are described e.g. in EP-A 189 230, EP-A 527 176, EP-A 1 154 243, EP-A 1 158 289, EP-A 1 223 412, EP-A 1 296 128, U.S. Pat. Nos. 4,524,610, 4,768, 384, 4,801,897, 4,823,614, 5,231,884, 5,359,881, 5,602,345, 5,661,232, 5,687,100, 6,006,609, 6,327,915, 6,343,517, 6,354,154, 6,487,917, 6,513,393, 6,634,241, US-A 2003/0154804, US-A 2003/0097881, US-A 2003/0097884, WO-A 88 02 476, WO-A 95/16 897, WO-A 01/02813, WO-A 01/02816, WO-A 02/099363, WO-A 03/048693. Especially, in U.S. Pat. Nos. 6,634,241, 6,487,917, 6,354,154, 6,343,517, 6,327,915, vibration-type measurement pickups, especially Coriolis mass flow pickups, are shown, which, in each case, include:

at least one measuring tube for the conveying of a fluid, which measuring tube has an inlet end and an outlet end and vibrates at least at times, wherein the measuring tube, for enabling the fluid to flow through the measuring tube, communicates, via a first tube segment opening into the inlet end and via a second tube segment opening into the outlet end, with a pipeline connected therewith, and wherein the measuring tube executes, during operation, mechanical oscillations about an imaginary oscillation axis connecting the two tube segments; and a support element for the oscillatable holding of the measuring tube, having a first end piece containing a passageway for the securement of the first tube segment and having a second end piece containing a passageway for the securement of the second tube segment;

wherein each of the two tube segments extends through its respective one of the passageways and each of the two passageways has an inner diameter, which is greater than an outer diameter of its associated tube segment, so that an intermediate space is formed between each of the associated tube segments and end pieces.

Additionally, measurement pickups of the described type include an exciter mechanism electrically connected with a corresponding measuring device electronics and serving for the driving of the at least one measuring tube. The exciter mechanism includes an oscillation exciter, especially an electrodynamic, or electromechanical, oscillation exciter, mechanically acting on the measuring tube. Such measurement pickups also include a sensor arrangement for delivering oscillation measurement signals. The sensor arrangement includes at least two sensor elements spaced from one another for reacting to vibrations of the measuring tube. During operation, the exciter mechanism is so actuated in suitable manner by the measuring device electronics by means of corresponding exciter signals, that the measuring tube executes, at least temporarily, vibrations, especially bending oscillations. For the sake of completeness, it is noted here that the illustrated support elements are usually completed to form a measurement pickup housing, which houses the at least one measuring tube, together with the oscillation exciters and sensors arranged thereon, as well as possible other components of the measurement pickup.

In principle, such measurement pickups, or transducers, come with two types of tube geometries, namely, on the one hand, straight measuring tubes and, on the other hand, bent measuring tubes, among which the U-shaped, or U-like, tubes are preferred tube shapes. Especially in the case of Coriolis pickups measuring mass flow, for reasons of symmetry, both types of tube geometries are most often used in the form of two measuring tubes extending in two parallel planes parallel to one another and, most often, also both containing fluid flowing through, naturally, also in parallel. For the one of the two variants having two parallel, straight tubes, reference can be made to, for example, U.S. Pat. Nos. 4,768,384, 4,793,191 and 5,610,342, and, for the other variant having two parallel, especially identically formed, U-shaped tubes, reference can be made e.g. to U.S. Pat. No. 4,127,028. Besides these types of mass flow pickups of double measuring tube arrangement working on the Coriolis principle, another type of measurement pickup has long been established in the market, namely those with a single straight or bent measuring tube. Measurement pickups of this type are described e.g. in U.S. Pat. Nos. 4,524,610, 4,823,614, 5,253,533, 6,006,609 or WO-A 02/099363.

For the case in which the measurement pickup being used involves one with a single, straight, measuring tube, the measurement pickup further includes a counter-oscillator affixed to the measuring tube and suspended, especially oscillatably, in the measurement pickup housing. The counter-oscillator serves, apart from holding the oscillation exciter and the sensor elements, for oscillatory decoupling of the vibrating measuring tube from the connected pipeline. This compensation cylinder can, in such case, be embodied e.g. as a tubular compensation cylinder, or box-shaped support frame, arranged coaxially with the measuring tube. To the referenced ensemble of features of the individual, above-described measurement pickups can also be added that a straight measuring tube, or the straight measuring tubes, as the case may be, is/are preferably made of pure titanium, a titanium alloy of high titanium content, pure zirconium or a zirconium alloy of high zirconium content, since, compared to measuring tubes of stainless steel, which is, per se, possible for straight measuring tubes, shorter installed lengths result, while a bent measuring tube, or bent measuring tubes, as the case may be, is/are preferably made of stainless steel, although titanium or zirconium, or their alloys, are also possible, in such case, as material of the measuring tubes.

In the case of inline measuring devices of the described kind, which are applied as Coriolis mass flow meters, their measuring device electronics determine, in operation, among other things, a phase difference between the two oscillation measurement signals delivered from the sensor elements and issue at their outputs a measurement signal derived therefrom, which presents a measured value corresponding with the behavior, over time, of the mass flow rate. If, as is usual for such inline measuring devices, also the density of the medium is to be measured, then the measuring device electronics determines additionally on the basis of the oscillation measurement signals an instantaneous oscillation frequency of the measuring tube. Moreover, also, for example, the viscosity of the medium can be measured on the basis of the power, especially a corresponding exciter current, for the exciter mechanism needed to maintain the oscillations of the measuring tube.

Besides the possibility of simultaneous measurement of a plurality of such process variables, especially mass flow, density and/or viscosity, by means of one and the same measuring device, there is another, significant advantage of inline measuring pickups of vibration-type, that they exhibit, among other things, a very high accuracy of measurement coupled with relatively little susceptibility to disturbances. Beyond this, such measuring devices can be used for practically any flowable medium and practically in any area of application in measurement and automation technologies.

In the manufacture of such measurement pickups of vibration-type, as already discussed in detail in U.S. Pat. Nos. 5,610,342, 6,047,457, 6,168,069, 6,598,281, 6,634,241 or also WO-A, the securement of the measuring tube within the support element, be it by welding, brazing, soldering and/or pressing, can be a special problem, especially with regard to the stability of the zero point and/or the availability of the measurement pickup. Additionally, as perceivable from U.S. Pat. Nos. 6,047,457, 6,168,069, 6,598,281, 6,634,241 or 6,523,421, considerable problems can also arise in the securement of the measuring tube inside of the support element, when measuring tube and support element are of different materials, for example titanium and high-grade steel, especially high-grade stainless steel.

As, furthermore, explained in, among others, also in U.S. Pat. Nos. 5,610,342, 6,047,457 or WO-A 03/048693, a suitable solution of the problem can be realized by affixing the measuring tube terminally in the support element by force- and/or interlocking-fit, with this force and/or interlocking fit being brought about by means of cold forming of the end pieces and/or of the tube segments. Studies of measurement pickups manufactured in this way have, however, shown, that the usually different expansion characteristics of the above-mentioned end pieces and the tube segments of the measuring tube held therein can lead to the fact that the clamping forces exerted by the end pieces on the measuring tube fall, in the case of temperature fluctuations, especially in the case of possible temperature shocks, such as can arise e.g. in the case of regularly performed cleaning operations with extremely hot washing liquids, below a critical value. This can, in turn, mean that the end piece and measuring tube lose, because of thermally-related expansions, the mechanical contact brought about by the rolling and, consequently, the support element becomes rotatable about the above-mentioned oscillation axis, relative to the measuring tube. After that, especially in the case of measurement pickups executing, during operation, also torsional oscillations about the oscillation axis, with a slipping of the support being an event that is no longer, with certainty, out of the question, a replacement of the entire measuring device becomes practically unavoidable. Comparable effects have been discussed in this connection also in WO-A 03/048693 and U.S. Pat. No. 6,598,281.

SUMMARY OF THE INVENTION

Proceeding from the above-described disadvantages in the state of the art, such as accompany the methods used in conventional manner in the manufacture of measurement pickups of the described kind for the securing of measuring tubes in support elements, an object of the invention is to improve measurement pickups of vibration-type in the direction such that a mechanically high strength and mechanically highly loadable, mechanical connection can be created between measuring tube and support element, as much as possible, without use of welded, brazed or soldered connections.

To achieve such object, the invention resides in a measurement pickup of vibration-type, especially one for producing mass flow dependent, Coriolis forces and/or for producing viscosity-dependent, frictional forces in flowing fluids. The measurement pickup of the invention includes at least one measuring tube exhibiting an inlet end and an outlet end and vibrating, at least at times, for communicating, via a first tube segment opening into the inlet end and via a second tube segment opening into the outlet end, with a connected pipeline for permitting flow-through of the fluid to be measured, as well as a support element for the oscillatable holding of the measuring tube, with the support element having a first end piece exhibiting a passageway for the affixing of the first tube segment and a second end piece exhibiting a passageway for the affixing of the second tube segment, wherein the measuring tube executes, during operation, mechanical oscillations about an imaginary axis of oscillation connecting the two tube segments, and wherein, in each case, one of the two tube segments extends through its own one of the two passageways and each of the two passageways has an inner diameter which is larger than an outer diameter of the, in each case, associated tube segment, so that, between each tube segment and end piece, an intermediate space is formed. The measurement pickup of the invention includes, further, at least one, especially metal, first spring element, which is pushed onto one of the two tube segments. The spring element fills the intermediate space formed between tube segment and end piece, with it being arranged in the intermediate space in such a manner that it contacts, at least sectionally, both the associated tube segment as well as also the associated end piece and in such a manner that it is subjected, at least sectionally, to radially acting, deformation forces. Due to the elastic deformation associated therewith, the spring element is held pressed against the associated tube segment and the associated end piece, whereby the given tube segment is locked securely in the associated passageway.

A basic idea of the invention is that the affixing of the measuring tube in the measurement pickup is implemented at least partially by means of a frictional connection, which can be assembled relatively easily, especially such as to be later releasable and, in the case of which, as required, can be easily implemented on the basis of standard connecting elements, such as e.g. annular springs, Spieth-sleeves, star-washers or the like.

A significant advantage of the invention is that, if required, a soldering, brazing or welding process for the affixing of the metal body on the measuring tube can be eliminated, since the action of pressure provides a very stable, mechanical connection between measuring tube and metal body. This is so strong, that, for practical purposes, the connection remains effective even after long-lasting bending- and/or torsional-oscillations of the measuring tube about the axis of oscillation.

By using a spring element elongated in the direction of the axis of oscillation, for example in the use of a spring packet composed of star-washers or a Spieth-sleeve, it is also possible to assure in simple manner that, in spite of a relatively high locking force acting over the clamping area formed by the spring packet, the lumen of the tube segments of the measuring tube is practically not constricted, even at these locations of clamping, and, consequently, the ideal circularly cylindrical form of the measuring tube lumen is kept essentially in tact. In any event, it is possible, without more, to assure that a decrease of the outer diameters of the tube segments possibly arising from the clamping force exerted by the spring elements is very slight compared to an elastic deformation of the installed spring element accompanying the enlargement of the inner diameter of the spring element. In other words, it can be arranged that the frictional connection is effected essentially by a change in the shape of the spring element, while the measuring tube remains at the same time essentially stable in form. As a result of this, deposits in the measuring tube can be effectively prevented that would form otherwise, under the right conditions during operation of the measurement pickup.

BRIEF DESCRIPTION OF THE DRAWINGS

The invention and other advantageous embodiments will now be explained on the basis of the figures of the drawing, in which—partially in perspective—different examples of embodiments are presented and in which equal parts are referenced with the same reference characters. The figures show as follows:

FIG. 2b is all exploded view, the parts of the measurement pickup shown in FIG. 2a.

DESCRIPTION OF THE PREFERRED EMBODIMENT

In a first embodiment of the measurement pickup of the invention, the spring element is embodied as a spring packet, which is composed of two, or more, leaf springs extending essentially radially with respect to the axis of oscillation and which, at least partially, so fills the intermediate space formed between tube segment and end piece. that the leaf springs contact both the associated tube segment and also the associated end piece.

In a second embodiment of the measurement pickup of the invention, the leaf springs are embodied essentially in the form of annular disks.

In a third embodiment of the measurement pickup of the invention, the leaf springs have an essentially star-shaped and/or meandering structure.

In a fourth embodiment of the measurement pickup of the invention, the leaf springs are provided with essentially radial slots.

In a fifth embodiment of the measurement pickup of the invention, the leaf springs are arranged one after the other in the direction of the axis of oscillation.

In a sixth embodiment of the measurement pickup of the invention, the leaf springs are composed of metal, especially spring steel.

In a seventh embodiment of the measurement pickup of the invention, a vibration-damping layer of plastic is provided between at least two leaf springs.

In an eighth embodiment of the measurement pickup of the invention, a clamping apparatus is provided for the leaf springs, with the clamping apparatus being connected, especially releasably, with the end piece and introducing deformation forces into the spring packet acting essentially in the direction of the axis of oscillation.

In a ninth embodiment of the measurement pickup of the invention, a second spring element is pushed onto the at least one tube segment, and a spacing ring is arranged between the two spring elements.

Figure 1:
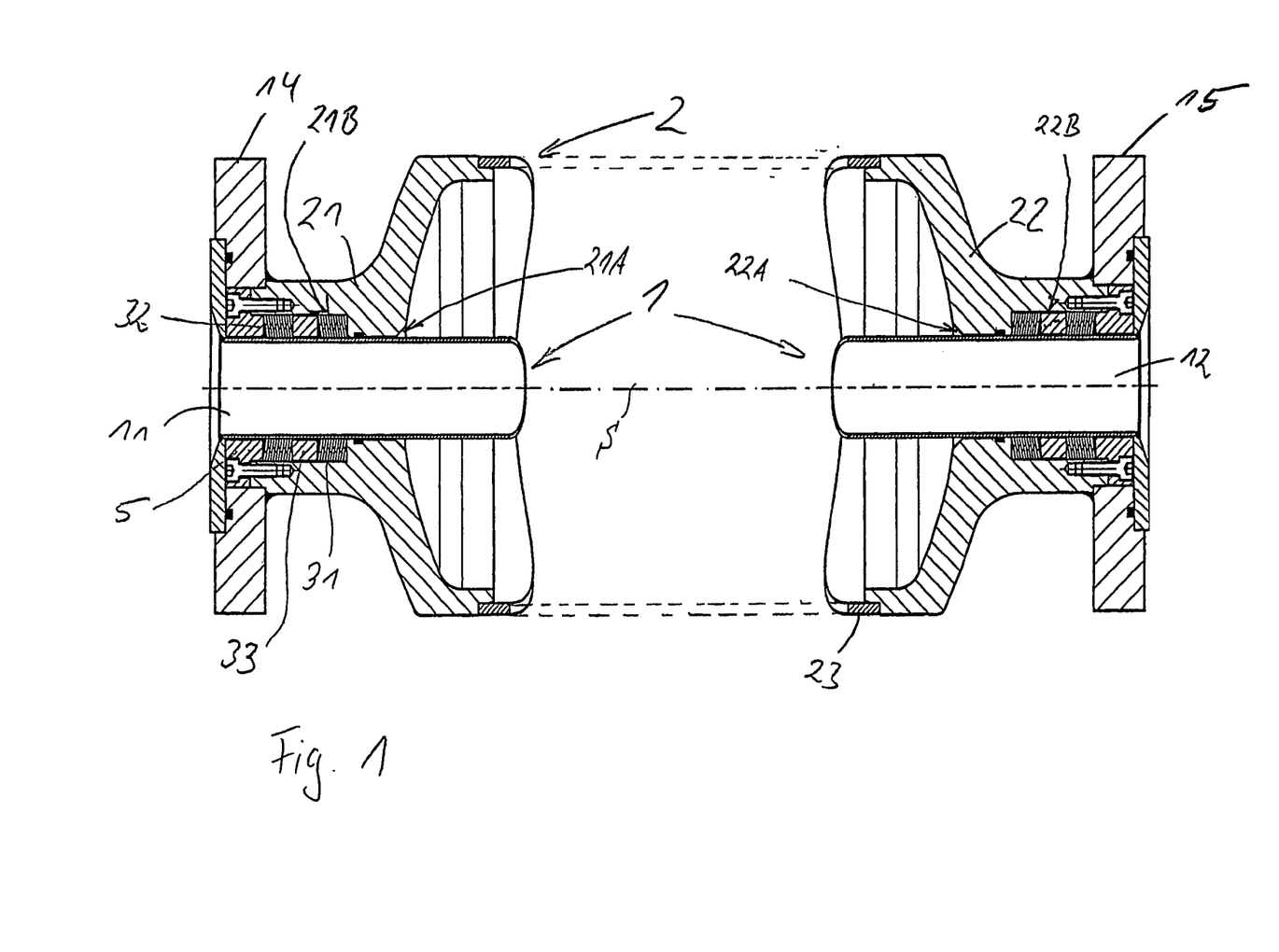
FIG. 1 in sectional view, for the invention, essential parts of an example of an embodiment of a measurement pickup of vibration-type, having at least one measuring tube.
Figure 2A:
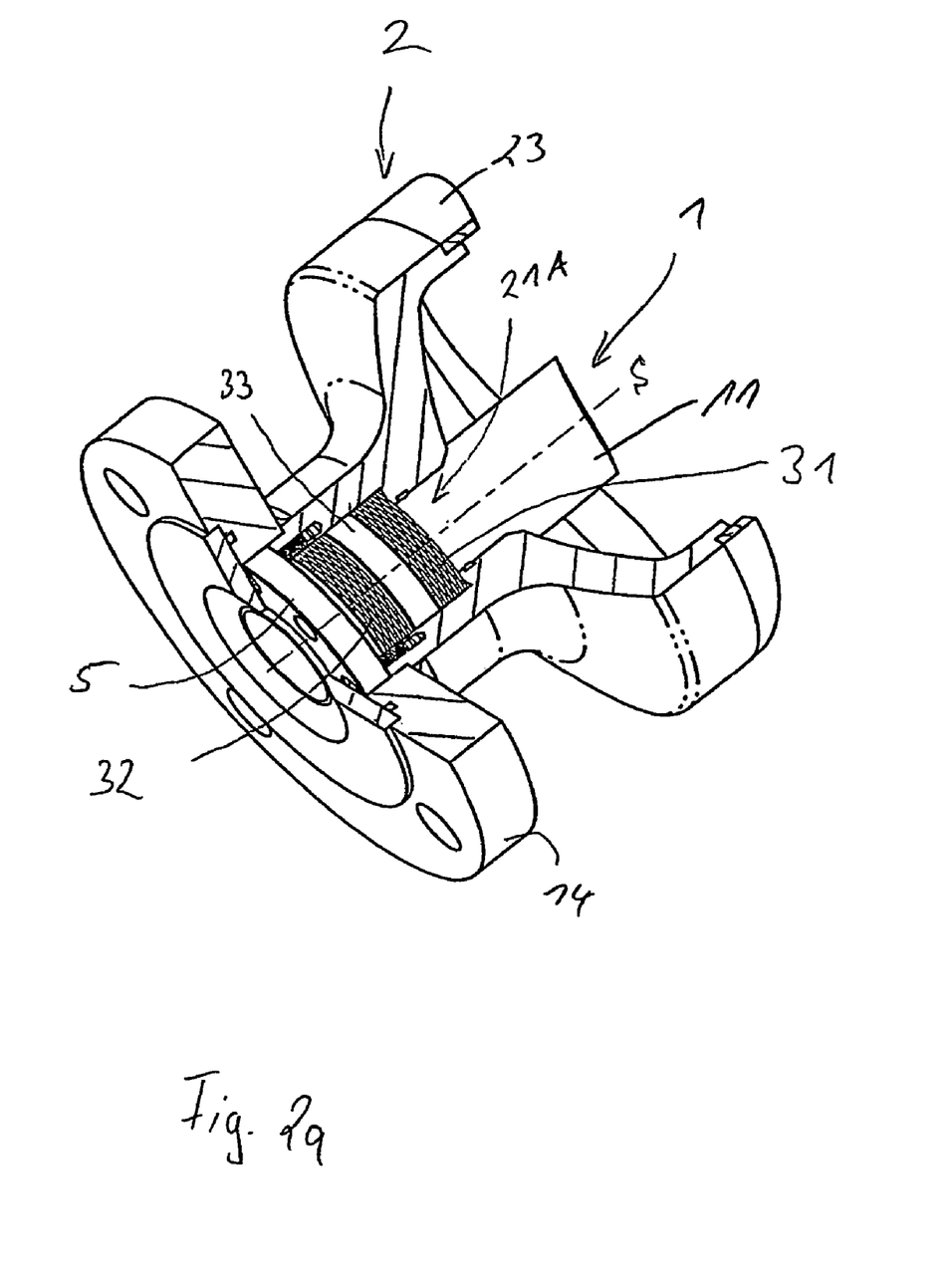
FIG. 2a is a partially sectional view, parts of the measurement pickup of FIG. 1.
Figure 2B:
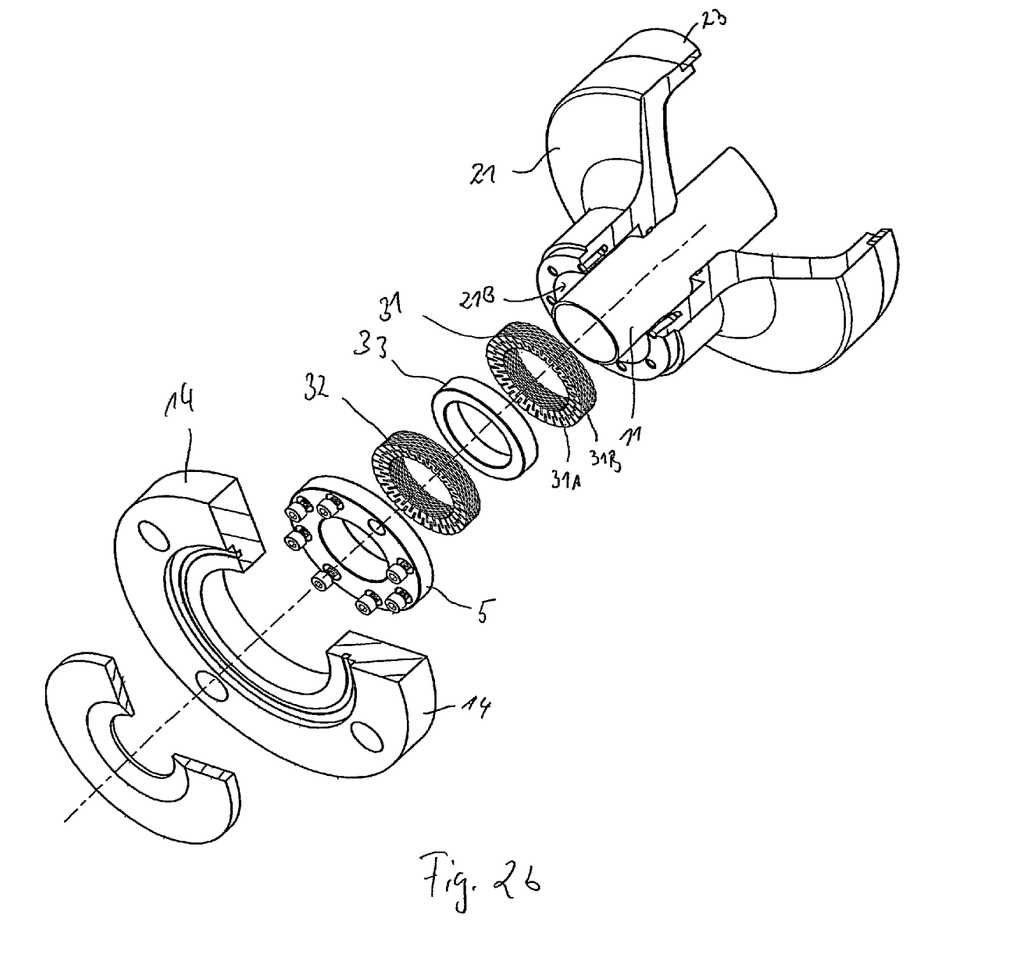

FIGS. 1, 2 and 2b show invention-essential parts of a measurement pickup, e.g. a Coriolis mass flow pickup, of vibration-type essential for the invention. Remaining parts likewise required for complete functioning are, for reasons of focusing on the present invention, not shown; for such not-shown features, reference is made to the documents mentioned above in the review of the state of the art.

The measurement pickup includes at least one measuring tube 1 having an inlet end and an outlet end. Measuring tube 1 is shown here with parts broken away and serves for conveying, during operation, a fluid to be measured, e.g. a liquid, a vapor or a gas. The measuring tube is inserted, during operation of the measurement pickup, into the course of a fluid-conveying pipeline, with the measuring tube 1 communicating with the connected pipeline to permit flow-through of the fluid via a first straight tube segment opening into the inlet end and via a second straight tube segment 12 opening into the outlet end. For the connecting of the measuring tube 1 to the pipeline, e.g. flanges 14, 15, or screwed connections or the like can serve in manner known to those skilled in the art. In operation of the measurement pickup, measuring tube 1 is caused to vibrate, at least at times, in order to produce fluid-describing, reaction forces, e.g. Coriolis forces correlated with mass flow rate and/or frictional forces correlated with viscosity. The measuring tube 1 executes, at least in part, mechanical oscillations about an imaginary oscillation axis S connecting the two tube segments 11, 12. For registering vibrations of measuring tube 1 and for producing oscillatory measurement signals corresponding with such, appropriate oscillation sensors (not shown) can be placed, in manner known to those skilled in the art, in the vicinity of the measuring tube 1.

Serving for the oscillatable holding of the measuring tube is a metal support element 2 connected with the measuring tube 1 at least via the two tube segments 11, 12 and, at least in part, encasing the measuring tube 1. Support element 2 can be e.g. box-shaped, or, as shown in FIGS. 2a, b, tubular.

Tube segment 11 is received by a passageway 21A of a first end piece 21. Passageway 21A extends along tube segment 11 essentially coaxially therewith. In turn, tube segment 12 is received by a passageway 22A of a second end piece 22, and passageway 22A extends along tube segment 12 essentially coaxially therewith. As shown in FIG. 1, the two end pieces 21, 22 are mechanically connected with one another outside of and over measuring tube 1 by means of at least one other, for example tubular or plate-shaped, connecting piece 23 of the support element 2. Each of the two passageways 21A, 22A has an inner diameter, which is greater than an outer diameter of its associated tube segment 11, 12, so that intermediate spaces 21B, 22B are formed between the pairs of tube segments 11, 12 and end pieces 21, 22.

Serving for the mechanical connection of tube segment 11 with the associated end piece 21 is at least a first spring element 31, which is pushed onto the tube segment 11. Spring element 31 is, in such case, arranged in such a manner in the intermediate space 21B that it contacts, at least sectionally, both the tube segment 11 and the end piece 21. To this end, spring element 31 is so embodied and so arranged in the intermediate space 21B, that it is subjected, at least sectionally, to radially acting deformation forces and held pressed against the associated tube segment 11 and the associated end piece 21 on the basis of the elastic deformations accompanying the deformation forces. Tube segment 11 is, therefore, essentially locked relative to the end piece 21. In this way, a mechanically high-strength and lasting frictional connection is provided between tube segment 11 and spring element 31, on the one hand, and between spring element 31 and end piece 21, on the other hand, such being very well suited for connecting the measuring tube, which, in operation, vibrates at high frequency, lastingly and securely with the support element 2.

For effecting the clamping forces required for deforming spring element 31, a clamping apparatus 5 is further provided, connected, especially releasably, with the end piece 21, for introducing into the spring element deformation forces acting essentially in the direction of the axis of oscillation S.

In an embodiment of the invention, the at least one spring element 31 is embodied in the form of a spring packet, composed of two or more leaf springs 31A, 31B, which extend essentially radially with respect to the oscillation axis S and which are arranged one after the other in the direction of the oscillation axis S. The spring packet fills, in such case, the intermediate space 21B between tube segment 11 and end piece 21, at least partially, such that the leaf springs 31A, 31B contact both the associated tube segment 11 and also the associated end piece 21. For further increasing the damping, thus for decreasing the mechanical quality of the spring packet, a vibration-damping layer of plastic can, for example, be placed between each two or more leaf springs 31A, 31B.

Figure 3A:
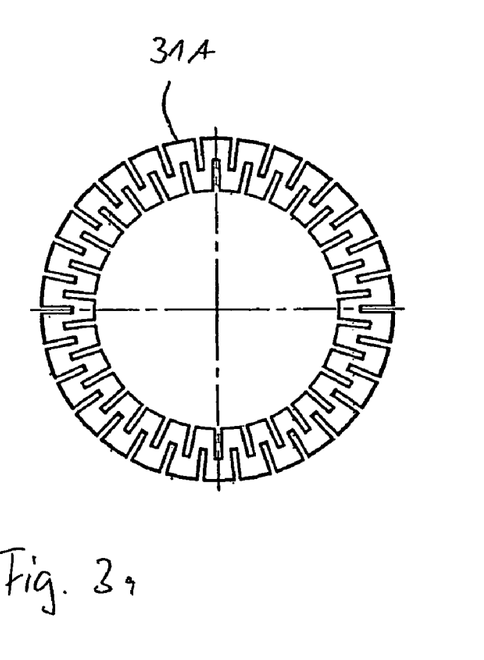
FIGS. 3a, b is a leaf spring suitable for the affixing of the measuring tube within the measurement pickup.
Figure 3B:
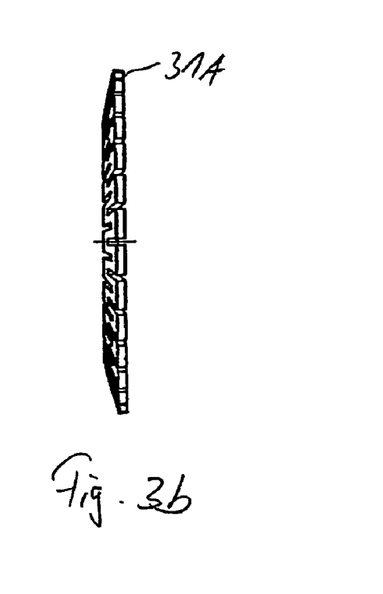

The leaf springs 31 are, in the shown example of an embodiment, formed essentially as annularly-shaped washers and provided with essentially radial slots, which are preferably so arranged, that the leaf springs 31A, 31B have an essentially star-shaped, or meandering, structure; compare FIGS. 2b, 3a, 3b. Such leaf springs 31A, 31B, especially such in the form of star washers, can also be procured as standard parts.

In a further embodiment of the invention, spring element 31 is embodied as a Spieth sleeve or as an annular-spring clamping-element.

In a further embodiment of the invention, especially for the case that the spring element 31 is in the form of a spring packet, a second spring element 32 is additionally provided, which is likewise pushed onto the tube segment 11 and forced to become locked against the end piece 21 in manner similar to that for spring element 31. In the case of this further development of the invention, as shown in FIGS. 1, 2a, b, there is placed between the two spring elements 31, 32 additionally an inflexible spacing ring 33. Spacing ring 33 is non-deformable in comparison with the two spring elements 31, 32, arranged essentially coaxially with the tube segment 11, movably in the measurement pickup, and serves for significantly increasing, in very simple manner, the holding forces and moments produced by the two spring elements 31, 32 in comparison to spring elements only placed in a row touching one another.

An essential advantage of the invention is to be seen in the fact that, in addition to keeping the advantages of the method for the manufacture of measurement pickups already described in U.S. Pat. No. 5,610,342, namely the affixing of the measuring tube 1 without welded, brazed or soldered connections and thus without thermal stresses, protectively to the support element 2, a considerable improvement of strength and, especially, also the permanence of the mechanical connection between measuring tube 1 and support element 2, can be achieved in very simple manner. Also, it is possible to assure that the measuring tube itself scarcely experiences any deformation, in spite of the high locking forces, with which it is held in support element 2, and, consequently, a largely uniform cross section is retained over the entire length of the measuring tube, even after installation.

The invention claimed is:

1. A Measurement pickup of vibration-type, comprising:
   at least one measuring tube for the conveying of a fluid, said measuring tube showing an inlet end and an outlet end and vibrating at least at times, said measuring tube communicates, via a first tube segment opening into said inlet end and via a second tube segment opening into said outlet end, with a pipeline connected therewith, said measuring tube executes mechanical oscillations about an imaginary oscillation axis connecting said two pipe segments; and
   a support element for oscillatable holding of said measuring tube, said support element showing a first end piece containing a passageway for the securement of said first tube segment and a second end piece containing a passageway for the securement of said second tube segment wherein:

each of said two tube segments extends through its respective one of the two passageways and each of the two passageways shows an inner diameter, which is greater than an outer diameter of its associated tube segment, so that an intermediate space is formed between each of the associated tube segments and end pieces, at least one of said two tube segments carries at least one, first spring element, and said first spring element is arranged in the intermediate space in such a manner that it contacts both its associated tube segment and also its associated end piece in such a manner that it is subjected to radially acting, deformation forces and, as a result of elastic deformations accompanying such, is held pressed against the associated tube segment and the associated end piece.

2. The measurement pickup as claimed in claim 1, wherein: said first spring element is embodied as a spring packet, which is composed of two or more leaf springs extending radially with respect to the oscillation axis, and which so fills the intermediate space formed between said first tube segment and said end piece that said leaf springs contact both the associated tube segment and the associated end piece.

3. The measurement pickup as claimed in claim 2, wherein: said leaf springs are embodied in the shape of annular washers.

4. The measurement pickup as claimed in claim 2, wherein: said leaf springs have a star-shaped structure.

5. The measurement pickup as claimed in claim 2, wherein: said leaf-springs are provided with radial slots.

6. The measurement pickup as claimed in claim 2, wherein: said leaf springs lie one after the other in the direction of the oscillation axis.

7. The measurement pickup as claimed in claim 2, further comprising:
a layer of vibration-damping plastic provided between said at least two leaf springs.

8. The measurement pickup as claimed in claim 2, wherein: said leaf springs show an essentially meandering structure.

9. The measurement pickup as claimed in claim 1, wherein: said first spring element is embodied as a Spieth-sleeve or as an annular-spring, locking element.

10. The measurement pickup as claimed in claim 1, further comprising:
a clamping apparatus, which is connected, with the at least one end piece, provided for said first spring element, which introduces into said first spring element deformation forces acting in the direction of the oscillation axis.

11. The measurement pickup as claimed in claim 1, further comprising;
a second spring element pushed onto said at least one tube segment; and
a spacing ring arranged between said two spring elements.

12. The measurement pickup as claimed in claim 1, wherein:
said first spring element is made of metal.

13. The measurement pickup as claimed in claim 1, further comprising:
a damping apparatus, which is connected releasably with the at least one end piece and is provided for said first spring element, said clamping apparatus introduces into said first spring element deformation forces acting essentially in the direction of the oscillation axis.

* * * * *